United States Patent
Desai

(10) Patent No.: US 9,737,553 B2
(45) Date of Patent: *Aug. 22, 2017

(54) CO-ADMINISTRATION OF STEROIDS AND ZOLEDRONIC ACID TO PREVENT AND TREAT OSTEOARTHRITIS

(71) Applicant: Levolta Pharmaceuticals, Inc., Bethlehem, PA (US)

(72) Inventor: Ketan Desai, Bethelehem, PA (US)

(73) Assignee: Levolta Pharmaceuticals, Inc., Bethlehem, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/514,042

(22) Filed: Oct. 14, 2014

(65) Prior Publication Data

US 2015/0031649 A1 Jan. 29, 2015

Related U.S. Application Data

(63) Continuation of application No. 14/202,950, filed on Mar. 10, 2014, now Pat. No. 8,859,530, which is a continuation-in-part of application No. 13/791,685, filed on Mar. 8, 2013, now Pat. No. 9,012,432.

(51) Int. Cl.
*A61K 31/675* (2006.01)
*A61K 31/573* (2006.01)
*A61K 45/06* (2006.01)

(52) U.S. Cl.
CPC .......... *A61K 31/675* (2013.01); *A61K 31/573* (2013.01); *A61K 45/06* (2013.01)

(58) Field of Classification Search
None
See application file for complete search history.

(56) References Cited

U.S. PATENT DOCUMENTS

| | | |
|---|---|---|
| 8,859,530 B2 | 10/2014 | Desai |
| 2003/0195171 A1 | 10/2003 | Daifotis et al. |
| 2004/0063670 A1 | 4/2004 | Fox et al. |
| 2005/0065117 A1 | 3/2005 | Lee |
| 2007/0048372 A1 | 3/2007 | Beyreuther et al. |
| 2009/0035315 A1 | 2/2009 | Christgau et al. |
| 2010/0158905 A1 | 6/2010 | Pearlman et al. |
| 2011/0263537 A1 | 10/2011 | Desai |
| 2014/0256682 A1 | 9/2014 | Desai |

OTHER PUBLICATIONS

Lockman Can. Fam. Physician. 2006 (52) 1403-1404.*
Arroll et al. British Medical Journal published Mar. 23, 2004.*
Laslett, L. L. et al., "Zoledronic acid reduces knee pain and bone marrow lesions over 1 year; a randomised controlled trial, Annals of the Rheumatic Diseases", Aug. 31, 2012, vol. 71, No. 8. pp. 1322-1328.
Jones, A. et al., "Intra-articular corticosteroids are effective in osteoarthritis but there are no clinical predictors of response", Annals of the Rheumatic Diseases, Nov. 30, 1996, vol. 55, No. 11, pp. 829-832.
Jul. 7, 2014 Notice of Allowance issued in U.S. Appl. No. 14/202,950 by Michael J. Schmitt.
Durnian, J., et al., "Bilateral acute uveitis and conjunctivitis after zoledronic acid therapy", "Eye (London)", Jul. 16, 2004, pp. 221-222, vol. 19, No. 2.
Di Lorenzo, G., et al., "Phase II Trial of Gemcitabine, Prednisone, and Zoledronic Acid in Pretreated Patients with Hormone Refractory Prostate Cancer", "Urology", 2007, pp. 347-351, vol. 69.
PDR 48th Edition, "Hydeltrason(R) Injection, Sterile (Prednisolone Sodium Phosphate), U.S.P.", "Physicians' Desk Reference", 1994, pp. 1460-1462.
Poznak, C., "The Use of Bisphosphonates in Patients With Breast Cancer", "Cancer Control", Nov./Dec. 2002, pp. 480-489, vol. 9, No. 6.
Marc C. Hochbert et al., "American College of Rheumatology 2012 recommendations for the use of nonpharmacologic and pharmacologic therapies in osteoarthritis of the hand, hip, and knee," Arthritis Care & Research, vol. 64, No. 4, Mar. 27, 2012, pp. 465-474.
Margareta Verdrengh et al.; "Addition of bisphosphonate to antibiotic and anti-inflammatory treatment reduces bone resorption in experimental *Staphylococcus aureus*-induced arthritis," Journal of Orthopaedic Research, vol. 25, No. 3, Mar. 1, 2007, pp. 304-310.
EP Search Report for Application No. 14761174.3 dated Jun. 30, 2016.

* cited by examiner

Primary Examiner — Jeffrey S Lundgren
Assistant Examiner — Michael Schmitt
(74) *Attorney, Agent, or Firm* — Andrews Kurth Kenyon LLP; David Bradin

(57) ABSTRACT

A combination therapy for treating osteoarthritis is disclosed. The combination therapy includes the co-administration of a steroid and Zoledronic Acid. The coadministration of a steroid decreases the production of cytokines, and, therefore, decreases the pro-inflammatory effects of Zoledronic Acid. The co-administration of Zoledronic Acid with steroids treats osteoarthritis, and helps to prevent the onset of osteoarthritis in patients at risk for osteoarthritis.

12 Claims, No Drawings

CO-ADMINISTRATION OF STEROIDS AND ZOLEDRONIC ACID TO PREVENT AND TREAT OSTEOARTHRITIS

CROSS REFERENCE TO RELATED APPLICATIONS

This application is a continuation under 35 USC 120 of U.S. patent application Ser. No. 14/202,950, filed Mar. 10, 2014, which is a continuation-in-part under 35 USC 120 of U.S. patent application Ser. No. 13/791,685, filed Mar. 8, 2013. The disclosures of U.S. patent application Ser. No. 13/791,685 and U.S. patent application Ser. No. 14/202,950 are hereby incorporated herein by reference in their entireties for all purposes.

FIELD OF THE INVENTION

The present invention relates to the method of use for the co-administration of steroids and Zoledronic Acid to prevent and treat osteoarthritis ("OA"). The steroid administration can be oral, parenteral, inhalational, or by suppository. The invention also patents a composition of matter whereby 7.5 mg of Methyl Prednisolone is mixed with 4 or 5 mg of Zoledronic Acid and infused in normal saline.

BACKGROUND OF THE INVENTION

Zoledronic Acid, sold as Zometa/Aclasta/Reclast, is a nitrogen containing bisphosphonate that is used for treatment of hypercalcemia of malignancy, for the treatment of bone metastasis associated with malignancies such as prostate and breast cancer, for the prevention of and treatment of osteoporosis and for the treatment of Paget's disease. Zoledronic Acid is administered by an intravenous infusion of 4 mg every 3-4 weeks (Zometa) for multiple myeloma and bone metastasis of other malignancies or 5 mg once a year (Aclasta/Reclast) for non-oncologyc indications. It is also used for the treatment of hypercalcemia of malignancy as needed.

Administration of Zoledronic Acid is complicated by what is described as "post-dosing syndrome" (PDS) which affects as much as 44% of patients as described in the Zometa Prescribing Information (http://www.pharma.us.novartis.com/product/pi/pdf/Zometa.pdf). The syndrome is characterized by fever, nausea, bone pain, arthralgia, myalgia, chills, etc. In addition, administration of Zoledronic Acid leads to worsening of arthralgia in persons suffering from osteoarthritis as described in Aclasta/Reclast/Zometa Prescribing Information. The etiology of this phenomenon has not been identified, but is associated with an increase in levels of tumor necrosis factor (TNF), interleukin 6 (IL-6), and gamma interferon (.gamma. IFN) (Dicuonzo G et al 2003, Schweitzer D H et al 1995, Thiebaud D et al 1997). These cytokines are usually produced by T cells. Zoledronic acid can cause stimulation of a subset of T cells known as gamma delta (y 6) T cells (Mariani S et al 2005). These cells, specifically V .gamma.9/V .gamma.2 T cells, can constitute up to 10% of circulating CD3 T cells when stimulated. Upon stimulation by Zoledronic Acid, these .gamma.6 T cells produce interleukin 2 (IL-2) and TNF. IL-2 in turn can stimulate the production of other cytokines such as IL-6 and .gamma.IFN. Thus, treatment with Zoledronic Acid can stimulate a subset of T cells that may lead to post-dosing syndrome by production and release of pro-inflammatory cytokines.

It would be advantageous to have compositions and methods for avoiding the onset of post-dosing syndrome. The present invention provides such compositions and methods.

Osteoarthritis (OA) is the most common bone and joint disease influenced by genetic and environmental factors. Osteoarthritis is a debilitating disorder, affecting millions of patients a year. Many therapeutics used to treat osteoarthritis have to be given on a daily basis, and in some cases, many times a day, in order to provide relief. The continued administration of these therapeutic agents, including non-steroidal anti-inflammatory drugs (NSAIDS), can result in liver disorders and gastro-intestinal perforations over time. In addition, they can cause impairment of renal function. Other measures to treat OA include direct injection into the knee joint of hyaluronic acid which causes relief for three to six months. It cannot be used in any other joint except the knee joint. Intra-articular steroids are used to treat OA, but they have a transient effect and are ineffective when given by any route other than by the intra-articular route. Thus, oral, intravenous, rectal, inhaled and topical steroids are not useful for treatment of OA. All intra-articular therapies have the side effect of pain during injection and possibilities of joint infection. All these medications treat pain, but do not have any effect on the disease. Thus, there is no disease modifying agent to treat OA. It would be advantageous to provide additional treatments for osteoarthritis, which can be given less frequently, have fewer side effects, and be effective. Finally, a disease modifying drug would be very useful. In addition to those patients identified as suffering from osteoarthritis, there are also patients that are at a high risk of osteoarthritis. There are accepted medical tests to identify such patients. For example, association studies have uncovered the genetic factors behind OA, its susceptibility genes, which enables physicians to predict disease occurrence based on genotype information. The predictive assays can screen for a single susceptibility gene, or, more preferably, a combination of susceptibility genes. However, there are few available preventative treatments for patients at risk of developing osteoarthritis.

It would further be advantageous to provide compositions and methods for preventing the onset of osteoarthritis in patients identified as being at risk of developing osteoarthritis.

The present invention provides such compositions and methods.

SUMMARY OF THE INVENTION

In one embodiment, the present invention relates to the co-administration of steroids and Zoledronic Acid to prevent or treat osteoarthritis. The steroids can be administered in oral (provided as a gel, capsule, tablet, powder, liquid, or other pharmaceutically acceptable form), intravenous, intramuscular, or inhaled form, as a suppository, or injected directly into a joint.

The co-administration of a steroid decreases the production of cytokines described above, and, therefore, decreases the pro-inflammatory effects of Zoledronic Acid. The co-administration of Zoledronic Acid with steroids treats osteoarthritis, and helps to prevent the onset of osteoarthritis in patients at risk for osteoarthritis. Existing osteoarthritis treatments are given frequently, for example, daily, or several times a day. In contrast, this combination can be given yearly, semi-yearly, quarterly, or monthly.

DETAILED DESCRIPTION

Compositions and methods for treating and preventing osteoarthritis are described. The compositions comprise Zoledronic acid and a steroid.

Zoledronic Acid

Zoledronic acid has the following formula:

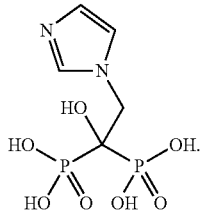

Zoledronic Acid is often administered as the bisphosphate, and can be administered in the form of a pharmaceutically-acceptable salt.

Analogs of Zoledronic acid are disclosed, for example, in U.S. Pat. No. 4,939,130, and these analogs are also intended to be within the scope of the invention, and can be used in place of Zoledronic Acid in each embodiment of the invention described herein. These analogs generally have the formula:

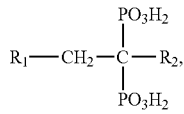

wherein $R_1$ is a 5-membered heteroaryl radical which contains, as hetero atoms, 2 to 4 N-atoms or 1 or 2 N-atoms as well as 1 O- or S-atom, and which is unsubstituted or C-substituted by lower alkyl, phenyl or phenyl which is substituted by lower alkyl, lower alkoxy and/or halogen, or by lower alkoxy, hydroxy, di-lower alkylamino, lower alkylthio and/or halogen, and/or is N-substituted at a N-atom which is capable of substitution by lower alkyl, lower alkoxy and/or halogen, and $R_2$ is hydrogen, hydroxy, amino, lower alkylthio or halogen.

Examples of 5-membered heteroaryl radicals containing 2 to 4 N-atoms or 1 or 2 N-atoms as well as 1 O- or S-atom as hetero atoms are: imidazolyl, e.g. imidazol-1-yl, imidazol-2-yl or imidazol-4-yl, pyrazolyl, e.g. pyrazol-1-yl or pyrazol-3-yl, thiazolyl, e.g. thiazol-2-yl or thiazol-4-yl, or, less preferably, oxazolyl, e.g. oxazol-2-yl or oxazol-4-yl, isoxazolyl, e.g. isooxazol-3-yl or isooxazol-4-yl, triazolyl, e.g. 1H-1,2,4-triazol-1-yl, 4H-1,2,4-triazol-3-yl or 4H-1,2,4-triazol-4-yl or 2H-1,2,3-triazol-4-yl, tetrazolyl, e.g. tetrazol-5-yl, thiadiazolyl, e.g. 1,2,5-thiadiazol-3-yl, and oxdiazolyl, e.g. 1,3,4-oxadiazol-2-yl. These radicals may contain one or more identical or different, preferably one or two identical or different, substituents selected from the group mentioned at the outset.

Radicals $R_1$, unsubstituted or substituted as indicated, are e.g. imidazol-2-yl or imidazol-4-yl radicals which are unsubstituted or C-substituted by phenyl or phenyl which is substituted as indicated, or which are C- or N-substituted by $C_{1-4}$ alkyl, e.g. methyl, and are typically imidazol-2-yl, 1-$C_{1-4}$ alkylimidazol-2-yl such as 1-methylimidazol-2-yl, or 2- or 5-$C_{1-4}$ alkylimidazol-4-yl such as 2- or 5-methylimidazol-4-yl, unsubstituted thiazolyl radicals, e.g. thiazol-2-yl, or 1H-1,2,4-triazol radicals, unsubstituted or substituted by $C_{1-4}$ alkyl such as methyl, e.g. 1-$C_{1-4}$ alkyl-1H-1,2,4-triazol-5-yl such as 1-methyl-1H-1,2,4-triazol-5-yl, or imidazol-1-yl, pyrazolyl-1-yl, 1H-1,2,4-triazol-1-yl, 4H-1,2,4-triazol-1-yl or tetrazol-1-yl radicals, unsubstituted or C-substituted by phenyl or phenyl which is substituted as indicated or by $C_{1-4}$ alkyl such as methyl, for example imidazol-1-yl, 2-, 4- or 5-$C_{1-4}$ alkylimidazol-1-yl such as 2-, 4- or 5-methylimidazol-1-yl, pyrazol-1-yl, 3- or 4-$C_{1-4}$ alkylpyrazol-1-yl such as 3- or 4-methylpyrazol-1-yl, 1H-1,2,4-tetrazol-1-yl, 3-$C_{1-4}$ alkyl-1H-1,2,4-triazol-1-yl such as 3-methyl-1H-1,2,4-triazol-1-yl, 4H-1,2,4-triazol-1-yl, 3-$C_{1-4}$ alkyl-4H-1,2,4-triazol-4-yl such as 3-methyl-4H-1,2,4-triazol-4-yl or 1H-1,2,4-tetrazol-1-yl.

Radicals and compounds hereinafter qualified by the term "lower" will be understood as meaning typically those containing up to 7 carbon atoms inclusive, preferably up to 4 carbon atoms inclusive. The general terms have for example the following meanings:

Lower alkyl is for example $C_{1-4}$ alkyl such as methyl, ethyl, propyl or butyl, and also isobutyl, sec-butyl or tert-butyl, and may further be $C_{5-7}$ alkyl such as pentyl, hexyl or heptyl.

Phenyl-lower alkyl is for example phenyl-$C_{1-4}$ alkyl, preferably 1-phenyl-$C_{1-4}$ alkyl such as benzyl.

Lower alkoxy is for example $C_{1-4}$ alkoxy such as methoxy, ethoxy, propoxy, isopropoxy, butoxy, isobutoxy, sec-butoxy or tert-butoxy.

Di-lower alkylamino is for example di-$C_{1-4}$ alkylamino such as dimethylamino, diethylamino, N-ethyl-N-methylamino, dipropylamino, N-methyl-N-propylamino or dibutylamino.

Lower alkylthio is for example $C_{1-4}$ alkylthio such as methylthio, ethylthio, propylthio or butylthio, and also isobutylthio, sec-butylthio or tert-butylthio.

Halogen is for example halogen having an atomic number of up to 35 inclusive, such as fluorine, chlorine or bromine.

Pharmaceutically acceptable salts of Zoledronic acid, or the other compounds of Formula I, include in particular the salts thereof with pharmaceutically acceptable bases, such as non-toxic metal salts derived from metals of groups Ia, Ib, IIa and IIb, e.g. alkali metal salts, preferably sodium or potassium salts, alkaline earth metal salts, preferably calcium or magnesium salts, copper, aluminium or zinc salts, and also ammonium salts with ammonia or organic amines or quaternary ammonium bases such as free or C-hydroxylated aliphatic amines, preferably mono-, di- or tri-lower alkylamines, e.g. methylamine, ethylamine, dimethylamine or diethylamine, mono-, di- or tri(hydroxy-lower alkyl) amines such as ethanolamine, diethanolamine or triethanolamine, tris(hydroxymethyl)aminomethane or 2-hydroxytert-butylamine, or N-(hydroxy-lower alkyl)-N,N-di-lower alkylamines or N-(polyhydroxy-lower alkyl)-N-lower alkylamines such as 2-(dimethylamino)ethanol or D-glucamine, or quaternary aliphatic ammonium hydroxides, e.g. with tetrabutylammonium hydroxide.

Zoledronic Acid, as well as the other compounds of Formula I may also be obtained in the form of inner salts, provided the group $R_1$ is sufficiently basic. These compounds can therefore also be converted into the corresponding acid addition salts by treatment with a strong protic acid such as a hydrohalic acid, sulfuric acid, sulfonic acid, e.g. methanesulfonic acid or p-toluenesulfonic acid, or sulfamic acid, e.g. N-cyclohexylsulfamic acid.

In one embodiment, Zoledronic Acid is administered as approved by the FDA, that is, by infusion, typically in infusions of around 4 to 5 mg infusions, once a year, or once every two years for post-menopausal women. In another embodiment, Zoledronic Acid is administered more frequently, for example, semi-yearly, quarterly, or monthly.

When administered as an infusion, the Zoledronic Acid is administered in a form suitable for intravenous administration to a human or other animal patient.

As used herein, "suitable for intravenous administration to a human or other animal patient" refers to an aqueous solution including rifalazil and one or more pharmaceutically acceptable excipients, such as salt, which forms a saline solution. Solutions that are suitable for intravenous administration to a human or other animal patient do not include excipients that would compromise the health of a patient. For example, certain organic solvents (e.g., dimethyl sulfoxide, ethanol, propanol, acetone, and dimethyl formamide) are miscible in water and useful for the preparation of aqueous solutions of insoluble compounds. However, these organic solvents are poisonous at certain concentrations, so should not be administered intravenously to a patient at harmful concentrations. Furthermore, solutions that are suitable for intravenous administration to a human typically have a pH of between 4 and 9. Accordingly, the solutions may be buffered as appropriate, for example, using phosphate-buffered saline.

By "infusion" is meant a continuous intravenous administration of Zoledronic Acid, or other compound of Formula I, or a pharmaceutically-acceptable salt thereof, over a period of greater than five minutes, wherein the compounds are ideally administered at a constant or near-constant rate.

In one aspect of this embodiment, patients are supplemented with calcium and/or vitamin D, if dietary intake is not sufficient. Whether or not supplementation is desired can be readily determined by a physician.

In another aspect of this embodiment, to prevent glucocorticoid-induced osteoporosis in patients expected to be on glucocorticoids for at least 12 months, Zoledronic Acid is administered in a 5 mg intravenous infusion once a year, given over no less than around 5 minutes, preferably no less than around 15 minutes. To prevent osteoporosis in post-menopausal women, the Zoledronic Acid is administered in a 5 mg intravenous infusion given once every 2 years intravenously over no less than 15 minutes. Accordingly, the frequency of dosing can be once every two years for post-menopausal women. Patients must be adequately supplemented with calcium and vitamin D if dietary intake is not sufficient. Postmenopausal women require an average of 1200 mg calcium and 800 to 1000 International Units of vitamin D daily.

However, in other embodiments, the Zoledronic Acid is administered by injection. Zoledronic Acid has a half-life (t1/2.alpha.) of about 0.24 hours, and its administration is known to be associated with certain side effects in a large subpopulation of patients. The co-administration of steroids helps to minimize or eliminate these side effects. By "co-administration," it is meant that the steroids can be administered within two hours before or after the Zoledronic acid, typically within one hour before or after the Zoledronic acid, and, more typically, at the same time, or within a half an hour before or after the Zoledronic Acid.

Steroids

Suitable steroids include, for example, hydrocortisone, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-valerate, acleometasone dipropionate, betamethasone valerate, betamethasone dippropionate, prednicarbate, clobetasone-17-butyrate, clobetasol-17-propionate, fluocortilone caproate, fluocortolone pivalate, and fluprednidene acetate, hydrocortisone-17-butyrate, 17-aceponate, 17-buteprate, and prednicarbate. The appropriate dose of steroid that is administered can be readily determined by one of skill in the art, for example, a treating physician. However, in one embodiment, the dose of steroids does not exceed the equivalent of 50 mg of prednisolone, and is not less than the equivalent of 5 mg of prednisone. The steroids can be given orally (for example, 7.5 mg of Prednisone), by a separate infusion (for example, 7.5 mg of Methyl Prednisolone), mixed in with Zoledronic Acid in the same infusion, or be administered intramuscularly, subcutaneously, by rectal suppository, by inhalation, or injected directly into a joint.

When considering a steroid to administer with the Zoledronic Acid or other compound of Formula I, or pharmaceutically-acceptable salt thereof, it is useful to note which are suitable for oral administration, and which are suitable for injection (whether intramuscular (IM) or intravenous (IV). The following table lists which steroids are suitable for oral administration and/or injection.

TABLE-US-00001 TABLE 1

| Steroid | Injectable (IM/IV) | Oral |
|---|---|---|
| Hydrocortisone | Y | Y |
| Hydrocortisone acetate | Y | Y |
| Cortisone acetate | Y | N |
| Tixocortol pivalate | T | Y |
| Prednisolone | Y | N |
| Methylprednisolone | Y | Y |
| Prednisone | Y | N |
| Triamcinolone acetonide | Y | Y |
| triamcinolone alcohol | Y | Y |
| mometasone | N | N |
| Amcinonide | N | N |
| Budesonide | Y | N |
| Desonide | n | N |
| fluocinonide | n | N |
| fluocinolone acetonide | N | N |
| Halcinonide | N | N |
| Betamethasone | Y | Y |
| Betamethasone sodium phosphate | N | Y |
| Dexamethasone | Y | Y |
| Dexamethasone sodium phosphate | N | N |
| Fluocortolone | N | N |
| Hydrocortisone-17-valerate | N | N |
| Aclometasone dipropionate | N | N |
| Betamethasone valerate | N | N |
| Betamethasone dippropionate | N | N |
| Prednicarbate | N | N |
| Clobetasone-17-butyrate | N | N |
| Clobetasol-17-propionate | N | N |
| Fluocortolone caproate | N | N |
| Fluocortolone pivalate | N | N |
| Fluprednidene acetate | ? | ? |
| Hydrocortisone-17-butyrate | N | N |
| 17-aceponate | ? | ? |
| 17-buteprate | N | N |
| prednicarbate | N | N |

Additional Therapeutic Agents

Additional therapeutic agents can be administered with the steroid and Zoledronic Acid. For example, analgesics and anesthetics can be administered. The anesthetic is any compound that is capable of blocking nerve impulses from the area of discomfort to the brain. Representative anesthetics include local anesthetics such as marcaine, procaine (novocaine), chloroprocaine (nesacaine), cocaine, lidocaine, tetracaine (amethocaine, pontocaine), mepivacaine, etidocaine (duranest), bupivacaine (marcaine), dibucaine (cinchocaine, nupercaine), prilocaine (citanest), benzoxinate (dorsacaine), proparacaine (alcaine, opthaine and opthetic), benzocaine (anesthesin), butamben (butesin), oxybuprocaine, pramoxine, proxymetacaine, and Alpha-2 adrenergic receptor agonists such as Dexmedetomidine and Propofol.

The choice of anesthetic will depend on the type of discomfort to be alleviated and is generally known to those skilled in the art of anesthesia. For example, lidocaine and marcaine are commonly injected, along with cortisone or hydrocortisone, directly into joints.

In addition to administration of additional therapeutic agents when the Zoledronic acid is administered, a patient can supplement the treatment by taking glycosaminoglycans, such as hyaluronic acid, glucosamine, chondroitin, and the like. These glycosaminoglycans are typically administered in an oral formulation, such as a pill, tablet, capsule, and the like, and hyaluronic acid can be injected along with the Zoledronic Acid, or pharmaceutically-acceptable salts thereof, and the steroid, directly into the knee, shoulder (particularly, the rotator cuff), the lumbar spine, and other joints, if desired.

Methods of Treatment

To treat a patient suffering from osteoarthritis, a patient can be administered a combination of Zoledronic Acid and a steroid. To obtain the maximum efficacy, the treatment should be initiated in patients with early stages of osteoarthritis ("OA") pathogenesis, or at least as early as possible.

The administration can be, for example, once a year. In one embodiment, the Zoledronic Acid and steroid are administered by simultaneous injection.

In one aspect of this embodiment, 7.5 mg of Methyl Prednisolone can be dissolved with about 4 to about 5 mg of Zoledronic Acid in an appropriate vehicle for injection, such as Normal Saline or Phosphate Buffered Saline (up to 100 cc) by swirling gently in room temperature for one minute. This mixture is ideally used within 5 minutes of mixing if kept at room temperature, or within an hour if kept in a refrigerator, so as to minimize the possibility of having a precipitate form.

In another embodiment, a steroid is given orally or via inhalation, and the Zoledronic Acid is given via infusion.

In another embodiment, a mixture of Zoledronic Acid or other compound of Formula I and a steroid is directly injected into a joint, such as a knee, shoulder, or hip joint. In this embodiment, the Zoledronic Acid and steroid can be combined with an anesthetic, or an anesthetic can be administered shortly before or after the combination of the Zoledronic Acid and steroid.

Representative anesthetics for this embodiment include lidocaine and marcaine

Representative steroids for this embodiment include cortisone, hydrocortisone, and pharmaceutically acceptable salts thereof Methods for Predicting the Onset of Osteoarthritis The methods described herein for treating osteoarthritis can also be used to prevent the onset of osteoarthritis for patients at risk of developing osteoarthritis.

To obtain the maximum efficacy, treatment should ideally be initiated when the patient is early stages of OA pathogenesis (see, for example, Yu et al., "Efficacy of zoledronic acid in treatment of osteoarthritis is dependent on the disease progression stage in rat medial meniscal tear model," Acta Pharmacol Sin. 2012 July; 33(7):924-34). Accordingly, it can be useful to identify patients at risk of developing osteoarthritis, and minimize the damage to their joints.

Numerous methods are described in the literature for predicting osteoarthritis, in man and in other mammals. These methods include, for example, assessments of joint mobility, and genetic testing using known alleles predictive of osteoarthritis. For example, methods for predicting osteoarthritis of the hip in Labrador retrievers are taught in Corfield, et al., "Assessment of the hip reduction angle for predicting osteoarthritis of the hip in the Labrador Retriever," Aust Vet J. 2007 June; 85(6):212-6. Methods for predicting osteoarthritis of the hip in humans are taught, for example, in Birrell et al., "Predicting radiographic hip osteoarthritis from range of movement," Oxford Journals Medicine Rheumatology, Volume 40, Issue 5 Pp. 506-512. Restriction in range of movement was predictive of the presence of OA in new presenters to primary care with hip pain, and the results of this examination can be used to inform decisions regarding treatment with the methods described herein.

Methods for predicting osteoarthritis of the knee are described, for example, in Takahashi et al., "Prediction model for knee osteoarthritis based on genetic and clinical information," Arthritis Research & Therapy 2010, 12:R187. Osteoarthritis (OA) is the most common bone and joint disease influenced by genetic and environmental factors. Recent association studies have uncovered the genetic factors behind OA, its susceptibility genes, which enable one to predict disease occurrence based on genotype information. The prediction can be based on the effects of only a single susceptibility gene, or using OA-prediction models based on more than one gene. Risk alleles that can be assessed include the three susceptibility genes, asporin (ASPN), growth differentiation factor 5 (GDF5), and double von Willebrand factor A domains (DVWA). Clinical information, as well as the number of risk alleles, can be used for OA prediction.

The present invention will be better understood with reference to the following non-limiting examples.

EXAMPLE 1

Treatment of Osteoporosis Patients with Zoledronic Acid and Steroids

Eight patients with osteoporosis were treated with a single infusion of Zoledronic Acid alone (four patients) or with a single infusion of the combination of prednisone and Zoledronic Acid (ZP, four patients). All four patients who received Zoledronic Acid suffered from PDS. In contrast, none of the patients receiving ZP suffered from PDS.

Of the 8 subjects, five had osteoarthritis. Of these five, three were treated with ZP and two with Zoledronic Acid. All three subjects treated with ZP had a decrease in joint pain (VAS scale) six months after the single infusion and one subject up to one year after the single infusion. In the Zoledronic Acid arm, both subjects had the same (one) or worse (one) level of pain than before the single infusion.

In a further study, this one, a single blind, single center study, 20 subjects with knee osteoarthritis were randomized to either intravenous ZP or ZA in a 1:1 ratio. Subjects were followed for six months. Efficacy was measured by change in pain in 100 mm visual analogue score (VAS) from baseline (mean values). Patients were asked about the level of pain without taking rescue medications (NSAIDS or tramadol). Bone mineral density (BMD) was determined at baseline and six months in order to detect any effect on bone.

The results are shown in Table 2 below:
TABLE-US-00002 TABLE 2 PDS (# Cohort reporting/total) .DELTA.BMD .DELTA. Mean VAS ZA 6/10 0-10 mm ZP 0/10 0-40 mm ZP was clearly more effective in controlling OA pain than ZA alone, with the added benefit of no post-dosing symptoms. The efficacy could not have been the result of Prednisolone, since IV Prednisolone by itself has no effect on arthritis pain, which is why steroids are not given orally or intravenously for osteoarthritis (only intra-articularly[2]).

In addition, the effect of Prednisolone is transient, less than a day, and so cannot account for the analgesic effect six months out. The effect of ZA was similar to that seen in the earlier study.

REFERENCES

1. Dicuonzo G, Vincenzi B, Santini D et al. Fever after Zoledronic acid administration is due to increase in TNF-alpha and IL-6. J Interferon Cytokine Res 2003; 23: 649-654.

2. Schweitzer D H, Oostendorp-van de Ruit M, Van der Pluijm G et al. Interleukin-6 and the acute phase response during treatment of patients with Paget's disease with the nitrogen-containing bisphosphonate dimethylaminohydroxyl-propylidene bisphosphonate. J Bone Miner Res 1995; 10: 956-962.
3. Thiebaud D, Sauty A, Burckhardt P et al. An in vitro and in vivo study of cytokines in the acute-phase response associated with bisphosphonates. Calcif Tissue Int 1997; 61: 386-392.
4. Mariani S, Muraro M, Pantaleoni F, Fiore F, Nuschak B, Peola S, et al. Effector T cells and tumor cells as immune targets of Zoledronic acid in multiple myeloma. Leukemia 2005; 18: 139-45.
5. Masoodi, Nasseer A. Oral Bisphosphonates and the Risk for Osteonecrosis of the Jaw. BJMP 2009:2(2) 11-15. June 2009).
6. Woo S B, Hellstein J W, and Kalmar J R. Systemic Review: Bisphosphonates and osteonecrosis of the jaws. Ann Intern Med 2006; 144:753-6.
7. Wilkinson G S, Kuo Y F, Freeman J L, Goodwin J S. Intravenous bisphosphonate therapy and inflammatory conditions or surgery of the jaw: a population based analysis. J Natl Cancer Institute 2007 Jul. 4; 99(13):1016-24.
8. Corfield, et al. Assessment of the hip reduction angle for predicting osteoarthritis of the hip in the Labrador Retriever. Aust Vet J. 2007 June; 85(6):212-6.
9. Birrell et al. Predicting radiographic hip osteoarthritis from range of movement. Oxford Journals Medicine Rheumatology, Volume 40, Issue 5 Pp. 506-512.
10. Takahashi et al. Prediction model for knee osteoarthritis based on genetic and clinical information. Arthritis Research & Therapy 2010, 12:R187

The contents of all references described herein are incorporated herein by reference in their entirety for all purposes.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

The invention claimed is:

1. A method of treating or preventing osteoarthritis, the method comprising administering a combination of a steroid and Zoledronic Acid or a pharmaceutically-acceptable salt thereof to a patient in need of treatment or prevention thereof.

2. A The method of treating osteoarthritis, the method comprising administering a combination of zoledronic acid and prednisolone to a patient in need of treatment thereof, wherein the method involves treating a patient suffering from osteoarthritis in the knee, shoulder, elbow, or back.

3. The method of claim 1, wherein the method involves administering the combination to a patient with risk factors indicating that they are or will be suffering from osteoarthritis.

4. The method of claim 1, wherein the Zoledronic Acid or a pharmaceutically-acceptable salt thereof is given via infusion or subcutaneously or orally or intramuscularly, and the steroid is given during, or between an hour before or after the Zoledronic Acid infusion.

5. The method of claim 1, wherein the Zoledronic Acid or a pharmaceutically-acceptable salt thereof is given via infusion or subcutaneously or orally or intramuscularly, and the steroid is given around between an hour before and an hour after the Zoledronic Acid infusion.

6. The method of claim 1, wherein the steroid is given orally, intravenously, subcutaneously, intramuscularly, by inhalation, by injection into a joint, or by a rectal suppository.

7. The method of claim 1, wherein the dose of the steroid is equivalent to between 5 mg and 50 mg of prednisolone.

8. A method for treating osteoarthritis in a joint, comprising administering a combination of a steroid, an anesthetic, and Zoledronic Acid directly into the joint.

9. The method of claim 8, wherein the joint is selected from the group consisting of knee, vertebrae, shoulder, hip, carpal, metacarpal, interphalengeal, tarsal, metatarsal, elbow, ankle, vertebral, and facetal joints.

10. The method of claim 8, wherein the steroid is selected from the group consisting of hydrocortisone, hydrocortisone acetate, cortisone acetate, tixocortol pivalate, prednisolone, methylprednisolone, prednisone, triamcinolone acetonide, triamcinolone alcohol, mometasone, amcinonide, budesonide, desonide, fluocinonide, fluocinolone acetonide, halcinonide, betamethasone, betamethasone sodium phosphate, dexamethasone, dexamethasone sodium phosphate, fluocortolone, hydrocortisone-17-valerate, acleometasone dipropionate, betamethasone valerate, betamethasone dipropionate, prednicarbate, clobetasone-17-butyrate, clobetasol-17-propionate, fluocortilone caproate, fluocortolone pivalate, and fluprednidene acetate, hydrocortisone-17-butyrate, 17-aceponate, 17-buteprate, and prednicarbate, or pharmaceutically-acceptable salts thereof.

11. The method of claim 8, wherein the anesthetic is lidocaine, marcaine, bupivacaine, pharmaceutically-acceptable salts thereof, or mixtures thereof.

12. The method of claim 8, where the anesthetic is selected from the group consisting of tetracaine, oxybuprocaine, benzocaine, butamben, dibucaine, pramoxine, proparacaine, proxymetacaine, cocaine, Dexmedetomidine and Propofol, or pharmaceutically- acceptable salts thereof.

* * * * *